United States Patent [19]

Tocker

[11] Patent Number: 5,229,356
[45] Date of Patent: Jul. 20, 1993

[54] SLOW RELEASE COMPOSITIONS COMPRISING HETEROCYCLIC SULFONYLUREA HERBICIDES, PARAFFIN WAX, HYDROCARBON POLYMERS, AND PARTICULATE FILLERS

[75] Inventor: Stanley Tocker, Wilmington, Del.

[73] Assignee: E. I. Du Ponte de Nemours and Company, Wilmington, Del.

[21] Appl. No.: 749,023

[22] Filed: Aug. 23, 1991

[51] Int. Cl.$^5$ .................. A01N 47/36; A01N 43/54; A01N 43/58; A01N 43/713
[52] U.S. Cl. ................... 504/214; 504/215; 71/DIG. 1
[58] Field of Search ............ 71/92, DIG. 1; 504/214, 504/215

[56] References Cited

U.S. PATENT DOCUMENTS 3,852,421 12/1974 Koyanagi et al. ............... 424/94
4,913,726 4/1990 Levitt ................................. 71/90

FOREIGN PATENT DOCUMENTS 40-25520 11/1965 Japan .
41-19080 11/1966 Japan .
 452200  1/1970 Japan .
52-47016 11/1977 Japan .
53-46888 12/1978 Japan .
62-277306 12/1987 Japan .
 2-288803 11/1990 Japan .

*Primary Examiner*—Allen J. Robinson
*Assistant Examiner*—S. Mark Clardy

[57] ABSTRACT

This invention relates to slow release granular compositions comprising one or more active herbicides and a process for their preparation.

7 Claims, No Drawings

SLOW RELEASE COMPOSITIONS COMPRISING HETEROCYCLIC SULFONYLUREA HERBICIDES, PARAFFIN WAX, HYDROCARBON POLYMERS, AND PARTICULATE FILLERS

BACKGROUND OF THE INVENTION

The invention relates to compositions comprising as the active ingredient one or more herbicides which are slowly released from said granular compositions.

Controlled release pesticidal compositions offer several possible advantages over conventional compositions. They are often preferred because fewer pesticide applications to the crop are necessary. Controlled release compositions offer safety to the environment by reducing pesticide overuse and run-off or soil (translocation) leaching into unwanted neighboring areas such as water ways and wells. They can also offer safety to the crop in instances when large doses of conventional formulations are phytotoxic and provide safety to workers applying pesticides in the field by reducing the toxicity of the pesticide. Finally, controlled release compositions allow the effective use of pesticides which are too rapidly degraded, volatilized or leached away by rain in conventional formulations (i.e., conventional pesticides with very low residual activity).

JP Hei 2[1990]-288,803 discloses a release-controlled granule containing a sulfonylurea, a barnyardgrass herbicide, a clay mineral, a paraffin wax and a surfactant.

SUMMARY OF THE INVENTION

This invention relates to a slow release herbicidal particulate composition comprising:

(1) One or more active ingredients selected from the group:
  (i) N-[[(4,6-dimethoxy-2-pyrimidinyl)amino]carbonyl]-1-methyl-4-(2-methyl-2H-tetrazole-5-yl)-1H-pyrazole-5-sulfonamide [Compound I];
  (ii) methyl 2-[[[[(4,6-dimethoxy-2-pyrimidinyl)amino]carbonyl]amino]sulfonyl]methyl]benzoate [Compound II or Londax ® herbicide]; and
  (iii) ethyl 5-[[[[(4,6-dimethoxy-2-pyrimidinyl)amino]carbonyl]amino]sulfonyl]-1-methyl-1H-pyrazole-4-carboxylate [Compound III];
(2) paraffin wax;
(3) synthetic or naturally occurring hydrocarbon polymer(s);
(4) a solid particulate filler; and
(5) optionally, an adjuvant such as a surfactant or dispersant; wherein the weight ratio of paraffin wax: hydrocarbon polymer ranges from 5:1; to 0.5:1; the weight ratio of active ingredient(s): paraffin wax and hydrocarbon polymer ranges from 1:25 to 1:0.25 and the filler ranges from 1 to 95% by weight of the total composition.

The adjuvants such as surfactants and dispersants are to adjust the release rate. The filler may include one or more fillers.

The particulate compositions of this invention can be used alone to control undesired vegetation. The particulate compositions of this invention are also useful in preparing granular compositions containing in addition other herbicidally active compounds with adjuvants known to be needed to prepare the granular compositions. The particulate compositions of this invention are preferably useful in the preparation of a granular composition for the control of weeds in rice comprising the present particulates, a herbicide useful for control of barnyardgrass and adjuvants.

Non-limiting examples of synthetic or naturally occurring polymers of the composition of the invention include ethylene/vinyl acetate copolymers (such as Elvax ®) or oxidized polyethylene polymer (such as Epolene ® E-10).

What is meant by solid particulate filler is any solid particles of 50 microns maximum, preferably below 25 microns, in particle size, examples of which include clay, calcium carbonate, calcium sulfate, calcium phosphate, barium sulfate, diatamaceous earth, talc and bentonite.

The size of the particles of the active ingredient is in the same size range given for the solid particulate filler.

Non-limiting examples of paraffin waxes of the composition of the invention include petroleum-type solid paraffin waxes, and crystalline compositions containing normal paraffin compounds and $C_{18}$-$C_{36}$ isoalkanes and cycloalkanes.

The compositions of the invention which are preferred for their ease of preparation and/or biological activity are:

(1) Compositions wherein the active ingredient is selected from the above Compounds I, II and III and the ratio of paraffin wax:hydrocarbon polymer ranges from 4:1 to 0.5:1;
(2) The composition of Preferred 1 wherein the ratio of active ingredient(s):paraffin wax/hydrocarbon polymer ranges from 1:10 to 1:2;
(3) The composition of Preferred 2 wherein the polymer is ethylene/vinylacetate copolymer or oxidized polyethylene;
(4) The composition of Preferred 3 wherein a surfactant is used;
(5) The composition of Preferred 4 wherein the filler is calcium carbonate.

This invention also relates to a process for preparing slow release pesticidal compositions wherein appropriate amounts of the active ingredient, paraffin wax and the polymer are mixed and heated to 60°–120° C., preferably 80°–100° C., and then the solid particulate filler is added, followed by cooling with agitation to room temperature to form a particulate. The resulting particulate composition may be applied directly or may be optionally mixed with other compositions known in the art containing one or more additional active ingredient followed by extrusion to prepare granules. The controlled release particulates can also be used to make other types of agricultural formulations such as liquid flowable products.

DETAILED DESCRIPTION OF THE INVENTION

This invention relates to particulate controlled release herbicide compositions for use in rice paddy fields for control of weeds. These novel compositions consist of:

1. A herbicide or mixture of herbicides;
2. Paraffin wax;
3. At least one higher melting polyhydrocarbon compatible with the wax above;
4. A solid particulate filler; and
5. Optionally, an adjuvant such as a surfactant or dispersant to adjust the release rate.

Various additional adjuvants can be used in quantities under 5% of the weight of the controlled release composition to adjust the release characteristics. In general, inorganic bases such as magnesium hydroxide and other water-soluble organic or inorganic particulates such as sugars tend to accelerate release. Water-soluble starches and polyacrylamides tend to make the release profile more linear with time as well as increase the release rate. Hydrophobic or oleophilic compounds such as stearic acid and stearates generally greatly reduce the release rate.

Although the particulate compositions of this invention are useful in particulate form they are also useful to prepare granular formulations by the further addition of porous or nonporous solid material, examples of which include sand, aggregated clays such as kaolinite, bentonite and attapulgite, vermiculite and granular salts or organic compounds such as sugars, urea, potassium or calcium carbonate, ammonium nitrate and other granular fertilizers and many inorganic salts. The present particulates may also be used to prepare granular formulations that also includes water-dispersible granules containing active ingredients, examples of which are Glean ® 75DF, Pinnacle ® DF and Londax ® 60 DF, products of E. I. du Pont de Nemours and Company, Wilmington, Del. Preferred granule size is about 150 to 4000 microns with 250 to 2000 microns being more preferred.

Two general granular products can be prepared from the particulate compositions of this invention. The process involves:
1. Granulating the compositions preferably in admixture with other actives and adjuvants such as dispersants and surfactants by known processes;
2. Overcoating the granular solids with a controlled release active particulate, using a binder.

The controlled release particulates could be used to prepare granular products containing complimentary pesticides also in controlled release form or as free or unencapsulated form, e.g., insecticides, fungicides or other herbicides. An especially valuable product was made involving commercial Londax ® (Du Pont), widely used to control weeds in rice, said product containing Compound II as the active ingredient and a controlled release particulate of Compound I. Compound is a complimentary sulfonylurea compound that is more efficacious than Compound II against perennial weeds, e.g., (Cyperus) and grasses found in rice paddy fields, and therefore provides a broader range of weed control than Compound II alone. However, in some geographic locations and climatic conditions, rice plants can be injured by Compound I. The major beneficial effects of the controlled released treatment of Compound I was to prolong its activity and reduce its phytotoxicity to the rice plants. Non-limiting examples of other suitable pesticides are listed below. The controlled release particulates of this invention consist of the pesticide in a protective matrix consisting of the aforementioned combination of a paraffin wax, hydrocarbon polymer and solid particulate filler. The preferred maximum particle size of the particulates of the invention is 420 microns, obtained by passing through a 35 mesh screen. The preferred maximum size for direct application or use in preparing of formulations, where suspendability in a liquid medium is required, is 25 microns. Reduction of particle size, if required, can be carried out by conventional milling techniques. In practice, however, the process of this invention produces controlled particulates primarily in the desired size range of 50 to 420 microns without milling.

Use of the polyhydrocarbon component in conjunction with paraffin wax confers much improved toughness and resistance to deformation by heat. Also, controlled release particulates using the components described above except for omission of such polymers tend to agglomerate at 50° C. during long term storage whereas similar compositions prepared with a barrier system containing 50% each of paraffin wax and a low molecular weight oxidized polyethylene (Eastman Kodak's Epolene ® E-10), for example, generally show no aggregation under such conditions.

The present slow release herbicidal particulate compositions are advantageous over slow release compositions of the art in that the form resulting from the present process is a particulate, not a granule. It is therefore not necessary to grind or mill the present compositions to the size needed in order to mix the ingredients with any desired additional ingredients that would or would not be subject to slow release. The compositions of the present invention advantageously can be used as a herbicide in particulate form or it can be granulated to form formulations that are totally in controlled release form or formulations having controlled release particulates of the invention with free or unencapsulated active ingredients.

The particulates of the present invention are further advantageous because they are physically stronger than prior art particulates and are better resistant to elevated temperatures without change in the release rate. The present slow release herbicidal particulate compositions are not possible without the inclusion of the hydrocarbon polymer. The use of wax alone without the hydrocarbon polymer does not usually produce a particulate. The absence of the solid particulate filler will not produce the particulates of the invention because of the agglomeration.

| Common Name | Chemical Name |
| --- | --- |
| acetochlor | 2-chloro-N-(ethoxymethyl)-N-(2-ethyl-6-methylphenyl)acetamide |
| acifluorfen | 5-[2-chloro-4-(trifluoromethyl)phenoxy]-2-nitrobenzoic acid |
| aclonifen | 2-chloro-6-nitro-3-phenoxybenzenamine |
| acrolein | 2-propenal |
| alachlor | 2-chloro-N-(2,6-diethylphenyl)-N-(methoxymethyl)-acetamide |
| alloxydim | methyl 2,2-dimethyl-4,6-dioxo-5-[1-[(2-propenyloxy)-amino]butylidene]cyclohexanecarboxylate |
| ametryn | N-ethyl-N'-(1-methylethyl)-6-(methylthio)-1,3,5-triazine-2,4-diamine |
| amitrole | 1H-1,2,4-triazol-3-amine |
| AMS | ammonium sulfamate |
| anilofos | S-[2-[(4-chlorophenyl)(1-methylethyl)amino]-2-oxoethyl] O,O-dimethylphosphorodithioate |

-continued

| Common Name | Chemical Name |
|---|---|
| asulam | methyl [(4-aminophenyl)sulfonyl]carbamate |
| atrazine | 6-chloro-N-ethyl-N'-(1-methylethyl)-1,3,5-triazine-2,4-diamine |
| aziprotryne | 4-azido-N-(1-methylethyl)-6-methylthio-1,3,5-triazin-2-amine |
| azoluron | N-(1-ethyl-1H-pyrazol-5-yl)-N'-phenylurea |
| barban | 4-chloro-2-butynyl 3-chlorocarbamate |
| benazolin | 4-chloro-2-oxo-3(2H)-benzothiazole acetic acid |
| benfluralin | N-butyl-N-ethyl-2,6-dinitro-4-(trifluoromethyl)-benzenamine |
| bensulfuron | 2-[[[[[(4,6-dimethoxy-2-pyrimidinyl)amino]methyl-carbonyl]amino]sulfonyl]methyl]benzoic acid, methyl ester |
| bensulide | O,O-bis(1-methylethyl) S-[2-[(phenylsulfonyl)amino]-ethyl]phosphorodithioate |
| bentazon | 3-(1-methylethyl)-(1H)-2,1,3-benzothiadiazin-4(3H)-one,2,2-dioxide |
| benzofluor | N-[4-(ethylthio)-2-(trifluoromethyl)phenyl]methane-sulfonamide |
| benzoylprop | N-benzoyl-N-(3,4-dichlorophenyl)-DL-alanine |
| benzthiazuron | N-2-benzothiazolyl-N'-methylurea |
| bialaphos | 4-(hydroxymethylphosphinyl)-L-2-aminobutanoyl-L-alanyl-L-alanine |
| bifenox | methyl 5-(2,4-dichlorophenoxy)-2-nitrobenzoate |
| bromacil | 5-bromo-6-methyl-3-(1-methylpropyl)-2,4(1H,3H)-pyrimidinedione |
| *bromobutide | (+)2-bromo-3,3-dimethyl-N-(1-methyl-1-phenylethyl)-butanamide |
| bromofenoxim | 3,5-dibromo-4-hydroxybenzaldhyde O-(2,4-dinitro-phenyl)oxime |
| bromoxynil | 3,5-dibromo-4-hydroxybenzonitrile |
| bromuron | N'-(4-bromophenyl)-N,N-dimethylurea |
| buminafos | dibutyl [1-(butylamino)cyclohexyl]phosphonate |
| butachlor | N-(butoxymethyl)-2-chloro-N-(2,6-diethylphenyl)-acetamide |
| butamifos | O-ethyl O-(5-methyl-2-nitrophenyl)-(1-methylpropyl)-phosphoramidothioate |
| buthidazole | 3-[5-(1,1-dimethylethyl)-1,3,4-thiadiazol-2-yl]-4-hydroxy-1-methyl-2-imidazolidinone |
| butralin | 4-(1,1-dimethylethyl)-N-(1-methylpropyl)-2,6-dinitrobenzenamine |
| butylate | S-ethyl bis(2-methylpropyl)carbamothioate |
| cacodylic acid | dimethyl arsinic oxide |
| carbetamide | (R)-N-ethyl-2-[[(phenylamino)carbonyl]oxy]-propanamide |
| CDAA | 2-chloro-N,N-di-2-propenylacetamide |
| CDEC | 2-chloroallyl diethyldithiocarbamate |
| chlomethoxyfen | 4-(2,4-dichlorophenoxy)-2-methoxy-1-nitrobenzene |
| chloramben | 3-amino-2,5-dichlorobenzoic acid |
| chlorbromuron | 3-(4-bromo-3-chlorophenyl)-1-methoxy-1-methylurea |
| chlorbufam | 1-methyl-2-propynl(3-chlorophenyl)carbamate |
| chlorfenac | 2,3,6-trichlorobenzeneacetic acid |
| chlorflurecol methyl | methyl 2-chloro-9-hydroxy-9H-fluorene-9-carboxylate |
| chloridazon | 5-amino-4-chloro-2-phenyl-3(2H)-pyridazinone |
| chlorimuron | 2-[[[[(4-chloro-6-methoxy-2-pyrimidinyl)-ethylamino]-carbonyl]amino]sulfonyl]benzoicacid, ethyl ester |
| chlornitrofen | 1,3,5-trichloro-2-(4-nitrophenoxy)benzene |
| chloropicrin | trichloronitromethane |
| chloroxuron | N'-[4-(4-chlorophenoxy)phenyl]-N,N-dimethylurea |
| chlorpropham | 1-methylethyl 3-chlorophenylcarbamate |
| chlorsulfuron | 2-chloro-N-[[(4-methoxy-6-methyl-1,3,5-triazin-2-yl)amino]carbonyl]benzenesulfonamide |
| chlorthal-dimethyl | dimethyl 2,3,5,6-tetrachloro-1,4-benzenedicarboxylate |
| chlorthiamid | 2,6-dichlorobenzene carbothioamide |
| chlortoluron | N'-(3-chloro-4-methylphenyl)-N,N-dimethylurea |
| cinmethylin | exo-1-methyl-4-(1-methylethyl)-2-[(2-methylphenyl)-methoxy]-7-oxabicyclo-[2.2.1]heptane |
| clethodim | (E,E)-(+)-2-[1-[[(3-chloro-2-propenyl)oxy]imino]-propyl]-5-[2-(ethylthio)propyl]-3-hydroxy-2-cyclohexen-1-one |
| clomazone | 2-[(2-chlorophenyl)methyl]-4,4-dimethyl-3-isoxazolidinone |
| cloproxydim | (E,E)-2-[1-[[(3-chloro-2-propenyl)oxy]imino]-butyl]-5-[2-(ethylthio)propyl]-3-hydroxy-2-cyclohexen-1-one |
| clopyralid | 3,6-dichloro-2-pyridinecarboxylic acid |
| CMA | calcium salt of MAA |
| cyanazine | 2-[[4-chloro-6-(ethylamino)-1,3,5-triazin-2-yl]amino]-2-methylpropanenitrile |
| cycloate | S-ethyl cyclohexylethylcarbamothioate |

-continued

| Common Name | Chemical Name |
|---|---|
| cycloxydim | 2-[1-ethoxyimino)butyl]-3-hydroxy-5-(tetrahydro-2H-thiopyran-3-yl)-2-cyclohexene-1-one |
| cycluron | 3-cyclooctyl-1,1-dimethylurea |
| cyperquat | 1-methyl-4-phenylpyridinium |
| cyprazine | 2-chloro-4-(cyclopropylamino)-6-(isopropylamino)-s-triazine |
| cyprazole | N-[5-(2-chloro-1,1-dimethylethyl)-1,3,4-thiadiazol-2-yl]cyclopropanecarboxamide |
| cypromid | 3',4'-dichlorocyclopropanecarboxanilide |
| dalapon | 2,2-dichloropropanoic acid |
| dazomet | tetrahydro-3,5-dimethyl-2H-1,3,5-thiadiazine-2-thione |
| DCPA | dimethyl 2,3,5,6-tetrachloro-1,4-benzenedicarboxylate |
| desmedipham | ethyl [3-[[(phenylamino)carbonyl]oxy]phenyl]-carbamate (methylthio)-s-triazine |
| diallate | S-(2,3-dichloro-2-propenyl)bis(1-methylethyl)-carbamothioate |
| dicamba | 3,6-dichloro-2-methoxybenzoic acid |
| dichlobenil | 2,6-dichlorobenzonitrile |
| dichlorprop | (+)-2-(2,4-dichlorophenoxy)propanoic acid |
| *diclofopmethyl | (+)-2-[4-(2,4-dichlorophenoxy)phenoxy]propanoic acid, methyl ester |
| diethatyl | N-(chloroacetyl)-N-(2,6-diethylphenyl)glycine |
| difenoxuron | N'-[4-(4-methoxyphenoxy)phenyl]-N,N-dimethylurea |
| difenzoquat | 1,2-dimethyl-3,5-diphenyl-1H-pyrazolium ion |
| diflufenican | N-(2,4-difluorophenyl)-2-(3-trifluoromethyl-phenoxy)pyridine-3-carboxamide |
| dimefuron | N'-[3-chloro-4-[5-(1,1-dimethylethyl)-2-oxo-1,3,4-oxadiazol-3(2H)-yl]phenyl]-N,N-dimethylurea |
| dimethachlor | 2-chloro-N-(2,6-dimethylphenyl)-N-(2-methoxy-ethyl)acetamide |
| dimethametryn | N-(1,2-dimethylpropyl)-N'-ethyl-6-(methylthio)-1,3,5-triazine-2,4-diamine |
| dimethipin | 2,3-dihydro-5,6-dimethyl-1,4-dithiin1,-1,4,4-tetraoxide |
| dimethylarsinic | dimethylarsinic acid |
| dinitramine | $N_3,N_3$-diethyl-2,4-dinitro-6-(trifluoromethyl)-1,3-benzenediamine |
| dinoseb | 2-(1-methylpropyl)-4,6-dinitrophenol |
| dinoterb | 2-(1,1-dimethylethyl)-4,6-dinitrophenol |
| diphenamid | N,N-dimethyl-α-phenylbenzeneacetamide |
| dipropetryn | 6-(ethylthio)-N,N'-bis(1-methylethyl)-1,3,5-triazine-2,4-diamine |
| diquat | 6,7-dihydrodipyrido[1,2-a:2',1'-c]pyrazinediium ion |
| diuron | N'-(3,4-dichlorophenyl)-N,N-dimethylurea |
| DNOC | 2-methyl-4,6-dinitrophenol |
| DPX-V9360 | 2-[[[(4,6-dimethoxypyrimidin-2-yl)aminocarbonyl]-aminosulfonyl]-N,N-dimethyl 3-pyridinecarboxamide |
| DSMA | disodium salt of MAA |
| dymron | N-(4-methylphenyl)-N'-(1-methyl-1-phenylethyl)urea |
| eglinazine-ethyl | N-[4-chloro-6-(ethylamino)-1,3,5-triazin-2-yl]glycine ethyl ester |
| endothall | 7-oxabicyclo[2.2.1]heptane-2,3-dicarboxylic acid |
| EPTC | S-ethyl dipropylcarbamothioate |
| ethalfluralin | N-ethyl-N-(2-methyl-2-propenyl)-2,6-dinitro-4-(trifluoromethyl)benzenamine |
| ethidimuron | N-[5-(ethylsulfonyl)-1,3,4-thiadiazol-2-yl]-N,N'-dimethylurea |
| *ethofumesate | (+)-2-ethoxy-2,3-dihydro-3,3-dimethyl5-benzofuranyl methanesulfonate |
| fenac | 2,3,6-trichlorobenzeneacetic acid |
| *fenoprop | (+)-2-(2,4,5-trichlorophenoxy)propanoic acid |
| *fenoxaprop | (+)-2-[4-[(6-chloro-2-benzoxazolyl)oxy]phenoxy]-propanoic acid |
| fenuron | N,N-dimethyl-N'-phenylurea |
| fenuron TCA | Salt of fenuron and TCA |
| flamprop-M isopropyl | 1-methylethyl N-benzoyl-N-(3-chloro-4-fluorophenyl)-D-alanine |
| flamprop-methyl | methyl N-benzoyl-N-(3-chloro-4-fluorophenyl)-DL-alaninate |
| *fluazifop | (+)-2-[4-[[5-(trifluoromethyl)-2-pyridinyl]oxy]-phenoxy]propanoic acid |
| fluazifop-P | (R)-2-[4-[[5-(trifluoromethyl)-2-pyridinyl]oxy]-phenoxy]propanoic acid |
| fluchloralin | N-(2-chloroethyl)-2,6-dinitro-N-propyl-4-(trifluoro-methyl)benzenamine |
| flumeturon | N,N-dimethyl-N'-[3-(trifluoromethyl)phenyl]urea |
| fluralin | N-butyl-N-ethyl-2,6-dinitro-4-(trifluoromethyl)-benzenamine |
| fluorodifen | p-nitrophenyl α,α,α-trifluoro-2-nitro-p-tolyl ether |
| fluoroglycofen | carboxymethyl 5-[2-chloro-4-(trifluoromethyl)-phenoxy]-2-nitrobenzoate |
| flurecol-butyl | butyl 9-hydroxy-9H-fluorene-9-carboxylate |

-continued

| Common Name | Chemical Name |
| --- | --- |
| fluridone | 1-methyl-3-phenyl-5-[3-(trifluoromethyl)phenyl]-4(1H)-pyridinone |
| flurochloridone | 3-chloro-4-(chloromethyl)-1-[3-(trifluoromethyl)phenyl]-2-pyrrolidinone |
| fluroxypyr | [(4-amino-3,5-dichloro-6-fluoro-2-pyridinyl)oxy]acetic acid |
| fomesafen | 5-[2-chloro-4-(trifluoromethyl)phenoxy]-N-(methylsulfonyl)-2-nitrobenzamide |
| fosamine-ammonium | ethyl hydrogen (aminocarbonyl)phosphonate ammonium ethyl |
| glufosinate-ammonium | ammonium 2-amino-4-(hydroxymethylphosphinyl)-butanoate |
| glyphosate | N-(phosphonomethyl)glycine |
| haloxyfop | 2-[4-[[3-chloro-5-(trifluoromethyl)-2-pyridinyl]oxy]-phenoxy]propanoic acid |
| hexaflurate | potassium hexafluoroarsenate |
| hexazinone | 3-cyclohexyl-6-(dimethylamino)-1-methyl-1,3,5-triazine-2,4(1H,3H)dione |
| imazamethabenz | 6-(4-isopropyl-4-methyl-5-oxo-2-imidazolin-2-yl)-m-toluic acid, methyl ester and 6-(4-isopropyl-4-methyl-5-oxo-2-imidazolin-2-yl)-p-toluic acid, methyl ester |
| imazapyr | (+)-2-[4,5-dihydro-4-methyl-4-(1-methylethyl)-5-oxo-1H-imidazol-2-yl]-3-pyridine-carboxylic acid |
| imazaquin | 2-[4,5-dihydro-4-methyl-4-(1-methylethyl)-5-oxo-1H-imidazol-2-yl]-3quinoline-carboxylic acid |
| imazethapyr | (+)-2-[4,5-dihydro-4-methyl-4-(1-methylethyl)-5-oxo-1H-imidazol-2-yl]-5-ethyl-3-pyridinecarboxylic acid |
| ioxynil | 4-hydroxy-3,5-diiodobenzonitrile |
| isocarbamid | N-(2-methylpropyl)-2-oxo-1-imidazolidine-carboxamide |
| isopropalin | 4-(1-methylethyl)-2,6-dinitro-N,N-dipropyl-benzenamine |
| isoproturon | N-(4-isopropylphenyl)-N',N'-dimethylurea |
| isouron | N'-[5-(1,1-dimethylethyl)-3-isoxazolyl]-N,N-dimethylurea |
| isoxaben | N-[3-(1-ethyl-1-methylpropyl)-5-isoxazolyl]-2,6-dimethoxybenzamide |
| karbutilate | 3-[[(dimethylamino)carbonyl]amino]phenyl-(1,1-dimethylethyl)carbamate |
| lactofen | (+)-2-ethoxy-1-methyl-2-oxoethyl 5-[2-chloro-4-(trifluoromethyl)phenoxy]-2-nitrobenzoate |
| lenacil | 3-cyclohexyl-6,7-dihydro-1H-cyclopenta-pyrimidine-2,4(3H,5H)-dione |
| linuron | N'-(3,4-dichlorophenyl)-N-methoxy-N-methylurea |
| MAA | methylarsonic acid |
| MAMA | monoammonium salt of MAA |
| MCPA | (4-chloro-2-methylphenoxy)acetic acid |
| MCPA-thioethyl | S-ethyl (4-chloro-2-methylphenoxy)ethanethioate |
| MCPB | 4-(4-chloro-2-methylphenoxy)butanoic acid |
| mecoprop | (+)-2-(4-chloro-2-methylphenoxy)propanoic acid |
| mefenacet | 2-(2-benzothiazolyloxy)-N-methyl-N-phenyl acetamide |
| mefluidide | N-[2,4-dimethyl-5-[[(trifluoromethyl)sulfonyl]amino]-phenyl]acetamide |
| metamitron | 4-amino-3-methyl-6-phenyl-1,2,4-triazin-5(4H)-one |
| metazachlor | 2-chloro-N-(2,6-dimethylphenyl)-N-(1(H)-pyrazol-1-ylmethyl)acetamide |
| methabenz-thiazuron | 1,3-dimethyl-3-(2-benzothiazolyl)urea |
| methal-propalin | N-(2-methyl-2-propenyl)-2,6-dinitro-N-propyl-4-(trifluoromethyl)benzenamide |
| metham | methylcarbamodithioic acid |
| methazole | 2-(3,4-dichlorophenyl)-4-methyl-1,2,4-oxadiazolidine-3,5-dione |
| methoxuron | N'-(3-chloro-4-methoxyphenyl)-N,N-dimethylurea |
| methoxyphenone | (4-methoxy-3-methylphenyl)(3-methylphenyl)-methanone |
| methyldymron | N-methyl-N'-(1-methyl-1-phenylethyl)-N-phenylurea |
| metobromuron | N'-(4-bromophenyl)-N-methoxy-N-methylurea |
| metolachlor | 2-chloro-N-(2-ethyl-6-methylphenyl)-N-(2-methoxy-1-methylethyl)acetamide |
| metaxuron | N'-(3-chloro-4-methoxyphenyl)-N,N-dimethylurea |
| metribuzin | 4-amino-6-(1,1-dimethylethyl)-3-(methylthio)-1,2,4-triazin-5(4H)-one |
| metsulfuron | 2-[[[[(4-methoxy-6-methyl-1,3,5-triazin-2-yl)-methylamino]carbonyl]amino]sulfonyl]benzoic acid, methyl ester |
| MH | 1,2-dihydro-3,6-pyridazinedione |
| molinate | S-ethyl hexahydro-1H-azepine-1-carbothioate |
| monalide | N-(4-chlorophenyl)-2,2-dimethylpentanamide |
| monolinuron | 3-(p-chlorophenyl)-1-methoxy-1-methylurea |
| monuron | N'-(4-chlorophenyl)-N,N-dimethylurea |

-continued

| Common Name | Chemical Name |
|---|---|
| MSMA | monosodium salt of MAA |
| naproanilide | 2-(2-naphthalenyloxy)-N-phenylpropanamide |
| napropamide | N,N-diethyl-2-(1-naphthalenyloxy)-propanamide |
| naptalam | 2-[(1-naphthalenylamino)carbonyl]benzoic acid |
| neburon | 1-butyl-3-(3,4-dichlorophenyl)-1-methylurea |
| nitralin | 4-methylsulfonyl-2,6-dinitro-N,N-dipropylaniline |
| nitrofen | 2,4-dichloro-1-(4-nitrophenoxy)benzene |
| nitrofluorfen | 2-chloro-1-(4-nitrophenoxy)-4-(trifluoromethyl)-benzene |
| norea | N,N-dimethyl-N'-(octahydro-4,7-methano-1H-inden-5-yl)urea 3aα,4α,5α,7α,7aα-isomer |
| norflurazon | 4-chloro-5-(methylamino)-2-[3-(trifluoromethyl)-phenyl]-3(2H)-pyridazinone |
| orbencarb | S-[2-(chlorophenyl)methyl]diethylcarbamothioate |
| oryzalin | 4-(dipropylamino)-3,5-dinitrobenzenesulfonamide |
| oxadiazon | 3-[2,4-dichloro-5-(1-methylethoxy)phenyl]-5-(1,1-dimethylethyl)-1,3,4-oxadiazol-2(3H)-one |
| oxyfluorfen | 2-chloro-1-(3-ethoxy-4-nitrophenoxy)-4-(trifluoromethyl)benzene |
| paraquat | 1,1'-dimethyl-4,4'-dipyridinium ion |
| pebulate | S-propyl butylethylcarbamothioate |
| pendimethalin | N-(1-ethylpropyl)-3,4-dimethyl-2,6-dinitro-benzenamine |
| perfluidone | 1,1,1-trifluoro-N-[2-methyl-4-(phenylsulfonyl)-phenyl]methanesulfonamide |
| phenisopham | 3-[[(1-methylethoxy)carbonyl]9 amino]phenyl ethylphenylcarbamate |
| phenmedipham | 3-[(methoxycarbonyl)amino]phenyl (3-methylphenyl)-carbamate |
| picloram | 4-amino-3,5,6-trichloro-2-pyridinecarboxylic acid |
| piperophos | S-[2-(2-methyl-1-piperidinyl)-2-oxoethyl]-O,O-dipropyl phosphorodithioate |
| pretilachlor | 2-chloro-N-(2,6-diethylphenyl)-N-(2-propoxyethyl)acetamide |
| procyazine | 2-[[4-chloro-6-(cyclopropylamino)-1,3,5-triazine-2-yl]amino]-2-methylpropanenitrile |
| prodiamine | 2,4-dinitro-N3,N3-dipropyl-6-(trifluoromethyl)-1,3-benzenediamine |
| profluralin | N-(cyclopropylmethyl)-2,6-dinitro-N-propyl-4-(trifluoromethyl)benzenamine |
| proglinazine-ethyl | N-[4-chloro-6-[(1-methylethyl)amino]-1,3,5-triazin-2-yl]glycine ethyl ester |
| prometon | 6-methoxy-N,N'-bis(1-methylethyl)-1,3,5-triazine-2,4-diamine |
| prometryn | N,N'-bis(1-methylethyl)-6-(methylthio)-1,3,5-triazine-2,4-diamine |
| pronamide | 3,5-dichloro-N-(1,1-dimethyl-2-propynyl)benzamide |
| propachlor | 2-chloro-N-(1-methylethyl)-N-phenyl-acetamide |
| propanil | N-(3,4-dichlorophenyl)propanamide |
| propaquizafop | 2-[[(1-methylethylidene)amino]oxy]ethyl 2-[4-[(6-chloro-2-quinoxalinyl)oxy]phenoxy]propanoate |
| propazine | 6-chloro-N,N'-bis(1-methylethyl)-1,3,5-triazine-2,4-diamine |
| propham | 1-methylethyl phenylcarbamate |
| propyzamide | 3,5-dichloro-N-(1,1-dimethyl-2-propynl)benzamide |
| prosulfalin | N-[[4-(dipropylamino)-3,5-dinitrophenyl]sulfonyl]-S,S-dimethylsulfilimine |
| prosulfocarb | S-benzyldipropylthiocarbamate |
| prynachlor | 2-chloro-N-(1-methyl-2-propynyl)acetanilide |
| pyrazon | 5-amino-4-chloro-2-phenyl-3(2H)-pyridazinone |
| pyrazosulfuron-ethyl | ethyl 5-[[[[(4,6-dimethoxy-2-pyrimidinyl)amino]-carbonyl]amino]sulfonyl]-1-methyl-1H-pyrazole-4-carboxylate |
| pyrazoxyfen | 2-[[4-(2,4-dichlorobenzoyl)-1,3-dimethyl-1H-pyrazol-5-yl]oxy]-1-phenylethanone |
| pyridate | O-(6-chloro-3-phenyl-4-pyridazinyl) S-octyl carbonothioate |
| quizalofop ethyl | (+)-2-[4-[(6-chloro-2-quinoxalinyl)oxy]phenoxy]-propanoic acid, ethyl ester |
| secbumeton | N-ethyl-6-methoxy-N'-(1-methylpropyl)-1,3,5-triazine-2,4-diamine |
| sethoxydim | 2-[1-(ethoxyimino)butyl]-5-[2-(ethylthio)propyl]-3-hydroxy-2-cyclohexen-1-one |
| siduron | N-(2-methylcyclohexyl)-N'-phenylurea |
| simazine | 6-chloro-N,N'-diethyl-1,3,5-triazine-2,4-diamine |
| simetryn | N,N'-diethyl-6-(methylthio)-1,3,5-triazine-2,4-diamine |
| sodium chlorate | sodium chlorate |
| sodium mono-chloroacetate | chloroacetic acid, sodium salt |
| sulfometuron | 2-[[[[(4,6-dimethyl-2-pyrimidinyl)amino]carbonyl]- |

-continued

| Common Name | Chemical Name |
| --- | --- |
| methyl | amino]sulfonyl]benzoic acid, methyl ester |
| 2,4,5-T | (2,4,5-trichlorophenoxy)acetic acid |
| 2,3,6-TBA | 2,3,6-trichlorobenzoic acid |
| TCA | trichloroacetic acid |
| tebutam | 2,2-dimethyl-N-(1-methylethyl)-N-(phenylmethyl)-propanamide |
| tebuthiuron | N-[5-(1,1-dimethylethyl)-1,3,4-thiadiazol-2-yl]-N,N'-dimethylurea |
| terbacil | 5-chloro-3-(1,1-dimethylethyl)-6-methyl-2,4(1H,3H)-pyrimidinedione |
| terbuchlor | N-(butoxymethyl)-2-chloro-N-[2-(1,1-dimethylethyl)-6-methylphenyl]acetamide |
| terbumeton | N-(1,1-dimethylethyl)-N'-ethyl-6-methoxy-1,3,5-triazine-2,4-diamine |
| terbuthylazine | 2-(tert-butylamino)-4-chloro-6-(ethylamino)-s-triazine |
| terbutol | 2,6-di-tert-butyl-p-tolyl methylcarbamate |
| terbutryn | N-(1,1-dimethylethyl)-N'-ethyl-6-(methylthio)-1,3,5-triazine-2,4-diamine |
| thifensulfuron | 3-[[[[(4-methoxy-6-methyl-1,3,5,-triazin-2-yl)amino]carbonyl]amino]sulfonyl]-2-thiophenecarboxylic acid, methyl ester |
| thiameturon-methyl | methyl 3-[[[[(4-methoxy-6-methyl-1,3,5-triazin-2-yl)amino]carbonyl]amino]sulfonyl]2-thiophene-carboxylate |
| thiazafluron | N,N'-dimethyl-N-[5-(trifluoromethyl)-1,3,4-thiadiazol-2-yl]urea |
| thiobencarb | S-[(4-chlorophenyl)methyl] diethylcarbamothioate |
| tiocarbazil | S-(phenylmethyl) bis(1-methylporpyl)carbamothioate |
| tralkoxydim | 2-[1-(ethoxyimino)propyl]-3-hydroxy-5-(2,4,6-trimethylphenyl)-2-cyclohexen-1-one |
| triallate | S-(2,3,3-trichloro-2-propenyl) bis(1-methylethyl)-carbamothioate |
| triasulfuron | 2-(2-chloroethoxy)-N-[[(4-methoxy-6-methyl-1,3,5-triazin-2-yl)amino]carbonyl]benzenesulfonamide |
| tribenuron methyl | 2-[[[[N-(4-methoxy-6-methyl-1,3,5-triazine-2-yl)-N-methylamino]carbonyl]amino]sulfonyl]benzoic acid, methyl ester |
| triclopyr | [(3,5,6-trichloro-2-pyridinyl)oxy] acetic acid |
| *tridiphane | (+)2-(3,5-dichlorophenyl)-2-(2,2,2-trichloroethyl)oxirane |
| trietazine | 6-chloro-N,N,N'-triethyl-1,3,5-triazine-2,4-diamine |
| trifluralin | 2,6-dinitro-N,N-dipropyl-4-(trifluoromethyl)-benzenamine |
| trimeturon | 1-(p-chlorophenyl)-2,3,3-trimethylpseudourea |
| 2,4-D | (2,4-dichlorophenoxy)acetic acid |
| 2,4-DB | 4-(2,4-dichlorophenoxy)butanoic acid |
| vernolate | S-propyl dipropylcarbamothioate |
| xylachlor | 2-chloro-N-(2,3-dimethylphenyl)-N-(1-methylethyl)-acetamide |

In the preparation of the samples shown below, the active material and additives were in a finely divided state, i.e., below 25 microns, and they were milled, if necessary, to achieve this. After the encapsulation process, the products were screened through a 35 mesh screen (500 microns). Most of the controlled release product was under 200 microns in size.

In the analysis work conducted to determine the cumulative amount of active released from the sample, sufficient sample was placed in pH7 buffered water to provide a total concentration of active of 30 parts per million. The aqueous mixtures were aged at room temperature. Aliquots were periodically taken which were filtered and the cumulative amount of active present was determined by HPLC using unmodified active as a control. Where the sulfonylurea was less soluble than 30 ppm, a smaller sample size was used, sufficient to provide a total of 2 ppm active.

The invention is further illustrated by the following examples wherein all parts and percentages are by weight unless otherwise indicated.

EXAMPLE 1

A mixture of 0.5 g powdered N-[[(4,6-dimethoxy-2-pyrimidinyl)-amino]carbonyl]-1-methyl-4-(2-methyl-2H-tetrazole-5-yl)-1H-pyrazole-5-sulfonamide (Compound I) and 1.3 g of a 1:1 melt blend of paraffin wax and oxidized polyethylene (Epolene® E-10, Eastman Kodak Co.) were heated with agitation to 100° C. in a forced air oven. Then, 7.0 g of solid particulate calcium phosphate (tribasio) which was preheated to 100° C. was added and the mixture was stirred until a homogenous mass resulted. Heating was discontinued and the mixture was stirred until room temperature was reached. The resultant particulate containing 5.6% active was screened through a 35 mesh screen and the release rate in pH 7 water was measured. In 17 hours, the cumulative amount released was 40%, in 136 hours, 65% was released and in 304 hours, 80% was released.

In simultaneous greenhouse tests, to determine the phytotoxicity of Compound I to rice, the above controlled release showed a reduction in damage to rice plants up to 50% when compared with the unmodified Compound I. In this experiment, the Compound I controlled release sample as well as unmodified Compound I were used at an application rate of 12 g a.i./HA, in conjunction with Compound II applied at an application rate of 24 g a.i./HA.

EXAMPLE 2

Using the same process as described in (1), except for the use of calcium carbonate instead of calcium phosphate (tribasic), a powdered blend was made of 0.5 g Compound I, 0.7 g 1:1 paraffin wax: Epolene ® E-10 and 2.0 calcium carbonate. The active content of Compound I was 15.2%. In 19 hours, 18% of the active compound was released; in 164 hours 61% was released, and in 331 hours 70% was released.

EXAMPLE 3

Using the procedure of Example 1, a particulate mixture of 0.5 g Compound I, 0.4 g paraffin wax, 0.4 g ethylene-vinyl acetate copolymer (Elvax ® 210, E. I. du Pont de Nemours and Company) and 3.0 g calcium carbonate was made. The product contained 11.62 g of the active compound. The cumulative release observed was 19% of the active compound in 17 hours, 55% in 113 hours and 79% in 304 hours.

EXAMPLE 4

Following the process of Example 1, except substituting a powdered urea-formaldehyde fertilizer for the mineral filler, a slow release composition was made in which the substrate has nutritive value and is biodegradable. The mixture consisted of 0.5 g Compound I, 0.4 g paraffin wax, 0.4 g Epolene ® E-10 and 3.0 g powdered urea-formaldehyde polymer. The urea-formaldehyde powdered polymer was prepared by mixing 37% aqueous formaldehyde, urea and water (in amounts that constitute 30%, 15% and 55% respectively), adjusting the pH to 3.0 with phosphoric acid, stirring for 2.5 hours at 25°–35° C., neutralizing with 30% aqueous ammonium hydroxide, filtering and drying in a forced air oven at 40°–50° C. The slow release herbicide particulate released 23% of the active compound in 17 hours, 59% in 136 hours and 79% in 376 hours.

EXAMPLE 5

Following the teaching of Example 1, controlled release particulate was prepared comprising 0.5 g methyl 2-[[[[(4,6-dimethoxy-2-pyrimidinyl)amino]carbonyl]amino]sulfonyl]methyl]benzoate (Compound II), 0.2 g of a 3:1 w:w blend of paraffin wax and Elvax ® 210 and 5.0 g calcium carbonate. The product contained 8.11% of Compound II, the slow release particulate prepared and released 20% of the active compound in 18 hours; 62% in 102 hours and 81% after 449 hours.

EXAMPLE 6

Following the process of Example 5, controlled release Compound II having a relatively broad range of release in about 430 hours was obtained by incorporating magnesium hydroxide in the matrix. Thus, a mixture was made of 0.5 g Compound II, 0.8 g of a 3:1 blend of paraffin wax and Elvax ® 210 0.2 g magnesium hydroxide and 4.8 g calcium carbonate. The mixture contained 7.59% active compound. The product release 16% of the active compound in 17 hours, 50% in 186 hours and 79% in 498 hours.

EXAMPLE 7

Using the procedure of Example 6, except substituting stearic acid for magnesium hydroxide, the following slower release pattern was observed: 9% of the active compound in 66 hours, 17% in 17 hours and 27% in 402 hours. This also showed that the rate of release could be adjusted by choice of adjuvants.

EXAMPLE 8

Using the process of Example 6 except substituting salicylic acid for magnesium hydroxide, faster release was observed. The product released 22% of the active compound in 66 hours and 75% in 402 hours.

EXAMPLE 9

This example relates to the formulation of granules containing two complimentary sulfonylureas, Compound II and Compound I for providing control of a broader range of weeds than either one alone. A mixture was made of 5.27 g methyl 2-[[[[(4,6-dimethoxy-2-pyrimidinyl)-amino]carbonyl]amino]sulfonyl]methyl]-benzoate Londax ® 60DF premix, and 2.0 g of the controlled release particulate of Example 1. To this was mixed in 1.14 g of water, and the resultant damp particulate mixture was forced through a 20 mesh screen. The resultant wet granules were dried in a forced air oven overnight at 40°–50° C. to give 600–750 granules containing 1.5% Compound I and 43.5% Compound II. The granular product released all of Compound II and 40% of Compound I in 17 hours.

What is claimed is:

1. A slow release herbicidal particulate composition for use in paddy rice comprising
   (1) One or more active ingredients selected from the group:
      (i) N-[[(4,6-dimethoxy-2-pyrimidinyl)amino]carbonyl]-1-methyl-4-(2-methyl-2H-tetrazole-5-yl)-1H-pyrazole-5-sulfonamide [Compound I];
      (ii) methyl 2-[[[[(4,6-dimethoxy-2-pyrimidinyl)amino]carbonyl]amino]sulfonyl]methyl]benzoate [Compound II or bensulfuronmethyl herbicide]; and
      (iii) ethyl 5-[[[[(4,6-dimethoxy-2-pyrimidinyl)amino]carbonyl]-amino]sulfonyl]-1-methyl-1H-pyrazole-4-carboxylate [Compound III];
   (2) paraffin wax; and
   (3) synthetic or naturally occurring hydrocarbon polymer(s); and
   (4) a solid particulate filler;
      wherein the weight ratio of paraffin wax: hydrocarbon polymer ranges from 5:1 to 0.5:1; the weight ratio of active ingredient(s): paraffin wax and hydrocarbon polymer ranges from 1:25 to 1:0.25 and the solid particulate filler ranges from 1 to 95% by weight of the total composition.

2. Compositions of claim 1 wherein the paraffin wax:hydrocarbon polymer ranges from 4:1 to 0.5:1.

3. The compositions of claim 2 wherein the active ingredients: paraffin wax and hydrocarbon polymer ranges from 1:10 to 1:1.5.

4. The compositions of claim 3 wherein the hydrocarbon polymer is a ethylene and vinylacetate copolymer or oxidized polyethylene.

5. The compositions of claim 4 wherein in addition a surfactant is included.

6. The compositions of claim 5 wherein the filler is calcium carbonate.

7. A process for preparing a slow release herbicidal composition comprising mixing:
   (1) Active ingredients selected from:

(i) N-[[(4,6-dimethoxy-2-pyrimidinyl)amino]carbonyl]-1-methyl-4-(2-methyl-2H-tetrazole-5-yl)-1H-pyrazole-5-sulfonamide [Compound I];

(ii) methyl 2-[[[[[4,6-dimethoxy-2-pyrimidinyl)amino]-carbonyl]amino]sulfonyl]methyl]benzoate [Compound II or Londax ® herbicide]; and (iii) ethyl 5-[[[[(4,6-dimethoxy-2-pyrimidinyl)amino]carbonyl]-amino]sulfonyl]-1-methyl-1H-pyrazole-4-carboxylate [Compound III];

(2) paraffin wax; and (3) synthetic or naturally occurring hydrocarbon polymer(s);

(4) a solid particulate filler;

wherein the weight ratio of paraffin wax: hydrocarbon polymer ranges from 5:1 to 0.5:1; the weight ratio of active ingredient(s): paraffin wax and hydrocarbon polymer ranges from 1:25 to 1:0.25, heating the mixture to 60°–120° C., adding the solid particulate filler in an amount that ranges from 1 to 95% by weight of the total composition and then cooling with agitation until the temperature reaches room temperature.

* * * * *